United States Patent [19]

Trova et al.

[11] Patent Number: 5,430,150

[45] Date of Patent: Jul. 4, 1995

[54] RETROVIRAL PROTEASE INHIBITORS

[75] Inventors: Michael P. Trova, Salisbury Mills; Robert E. Babine, Nanuet; Nan Zhang, Valley Cottage; Steven R. Schow, Washingtonville; Allan Wissner, Ardsley, all of N.Y.

[73] Assignee: American Cyanamid Company, Wayne, N.J.

[21] Appl. No.: 991,876

[22] Filed: Dec. 16, 1992

[51] Int. Cl.⁶ ................. C07D 217/18; C07D 217/14; C07D 217/12; A61K 31/47
[52] U.S. Cl. ..................................... 546/139; 546/141; 546/144; 546/146; 546/152; 546/153; 546/156; 546/164
[58] Field of Search ............... 546/139, 141, 144, 146, 546/152, 153, 156, 164; 514/307, 309, 311, 312, 314

[56] References Cited

U.S. PATENT DOCUMENTS

| | | | |
|---|---|---|---|
| 5,126,326 | 6/1992 | Anderson | 514/17 |
| 5,142,056 | 8/1992 | Kempe | 546/265 |
| 5,151,438 | 9/1992 | Sham | 514/357 |
| 5,196,438 | 3/1993 | Martin et al. | 546/164 |

FOREIGN PATENT DOCUMENTS

| | | |
|---|---|---|
| 337714 | 10/1989 | European Pat. Off. |
| 356223 | 2/1990 | European Pat. Off. |
| 0432695A2 | 6/1991 | European Pat. Off. |
| 0434365A2 | 6/1991 | European Pat. Off. |
| 434365 | 6/1991 | European Pat. Off. |
| 480714 | 4/1992 | European Pat. Off. |
| 0492136A2 | 7/1992 | European Pat. Off. |
| 0541168A1 | 5/1993 | European Pat. Off. |
| 541168 | 5/1993 | European Pat. Off. |
| WO93/09096 | 5/1993 | WIPO . |
| WO93/09132 | 5/1993 | WIPO . |

OTHER PUBLICATIONS

Stuart–Harris, C. H., The Background to Chemotherapy of Virus Diseases, pp. 76–77, 1964.
Roberts, et al., Science 1990, 248. 358–361.
Young J. Med. Chem, 1992, 35, 1702–1709.
Rich, J. Med. Chem, 1991, 34, 1225–1278.
Thompson, J. Med. Chem., 1992, 35, 1685–1701.
Ghosh. J. Org. Chem., 1993, 58. 1025–1029.
Ghosh. J. Org. Chem., 1991, 56, 6500–6503.
Evans, J. Med. Chem., 1985, 50, 4615–4675.
Fray, J. Org. Chem., 1986, 51, 4828–4833.
J. Med. Chem, vol. 34, No. 3, 1991 pp. 1228–1230, J. P. Vacca et al. "Benzocycloalkyl Amines as Novel C–Termini for HIB Protease Inhibitors".
Science vol. 248, 20 Apr. 1990, pp. 1228–1230, J. P. Vacca et al. "Rational Design of Peptide–Based HIB Proteinase Inhibitors".

*Primary Examiner*—C. Warren Ivy
*Assistant Examiner*—D. Margaret M. Mach
*Attorney, Agent, or Firm*—Thomas S. Szatkowski

[57] ABSTRACT

Compounds of the formula I:

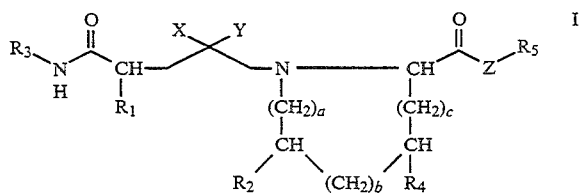

wherein X, Y, Z, a, b, c, $R_1$, $R_2$, $R_3$, $R_4$ and $R_5$ are defined in the specification are provided. The compounds are useful as inhibitors of retroviral protease enzymes.

6 Claims, 1 Drawing Sheet

FIG. 1

RETROVIRAL PROTEASE INHIBITORS

BACKGROUND OF THE INVENTION

1. Field of the Invention

The invention relates to novel compounds which are useful as inhibitors of retroviral protease enzymes and act as anti-HIV agents.

SUMMARY OF THE INVENTION

This invention is concerned with novel compounds of the formula I which are useful as inhibitors of retroviral protease enzymes and act as anti-HIV agents.

Compounds of the formula I:

wherein:

Z is a single bond, oxygen or NH;

X is hydroxyl and Y is hydrogen or —$CH_2OH$ or X and Y taken together may be an epoxide —($CH_2O$)—;

$R_1$ is hydrogen; straight or branched ($C_1$-$C_7$)alkyl; —($CH_2$)$_n$-cyclic($C_3$-$C_7$)alkyl, n=0-4; —($CH_2$)$_n$-phenyl, n=0-4; or —($CH_2$)$_n$-substituted phenyl, n=0-4, substituted with F, Cl, Br, I, ($C_1$-$C_4$)alkoxide, straight, branched or cyclic ($C_1$-$C_6$)alkyl or phenyl;

a, b and c are independently 0-3 provided that a+b+c is less than 4;

$R_2$ is hydrogen; hydroxyl; —Q-straight or branched ($C_1$-$C_7$)alkyl; —Q—($CH_2$)$_n$-cyclic($C_3$-$C_7$)alkyl, n=0-4; —Q—($CH_2$)$_n$-phenyl, n=0-4; or —Q—($CH_2$)$_n$-substituted phenyl, n=0-4, substituted with F, Cl, Br, I, ($C_1$-$C_4$)alkoxide, straight, branched or cyclic ($C_1$-$C_6$)alkyl; where Q is oxygen or a single bond;

$R_4$ is —Q-straight or branched ($C_1$-$C_7$)alkyl; —Q—($CH_2$)$_n$-cyclic($C_3$-$C_7$)alkyl, n=0-4; —Q—($CH_2$)$_n$-phenyl, n=0-4; or —Q—($CH_2$)$_n$-substituted phenyl, n=0-4, substituted with F, Cl, Br, I, ($C_1$-$C_4$)alkoxide, straight, branched or cyclic ($C_1$-$C_6$)alkyl; where Q is oxygen or a single bond; or $R_2$ and $R_4$ taken together are a moiety of the formula:

d, e and f are independently 0-3 provided that d+e+f is less than 4;

$R_{24}$ is hydrogen; hydroxyl; —Q-straight or branched ($C_1$-$C_7$)alkyl; —Q—($CH_2$)$_n$-cyclic($C_3$-$C_7$)alkyl, n=0-4; —Q—($CH_2$)$_n$-phenyl, n=0-4; or —Q—($CH_2$)$_n$-substituted phenyl, n=0-4, substituted with F, Cl, Br, I, ($C_1$-$C_4$)alkoxide, straight, branched or cyclic ($C_1$-$C_6$)alkyl; where Q is oxygen or a single bond;

$R_{42}$ is hydrogen; hydroxy; —Q-straight or branched ($C_1$-$C_7$)alkyl; —Q—($CH_2$)$_n$-cyclic($C_3$-$C_7$)alkyl, n=0-4; —Q—($CH_2$)$_n$-phenyl, n=0-4; or —Q—($CH_2$)$_n$-substituted phenyl, n=0-4, substituted with F, Cl, Br, I, ($C_1$-$C_4$)alkoxide, straight, branched or cyclic ($C_1$-$C_6$)alkyl; where Q is oxygen or a single bond; or when e=1 or 2, $R_{24}$ and $R_{42}$ may be taken together as a single bond whereby forming a 3 or 4 membered ring;

$R_3$ is a moiety of the formula:

wherein:

$R_6$ is a straight or branched ($C_1$-$C_7$) alkyl optionally substituted with cyclic ($C_3$-$C_7$) alkyl, —OH, —CON($R_1$)$_2$, heterocycle as defined hereinbelow, phenyl, or phenyl substituted with F, Cl, Br, I, ($C_1$-$C_4$) alkoxide, straight, branched or cyclic ($C_1$-$C_6$)alkyl; cyclic ($C_3$-$C_7$) alkyl; heterocycle as defined hereinbelow; phenyl; phenyl substituted with F, Cl, Br, I, ($C_1$-$C_4$) alkoxide, straight, branched or cyclic ($C_1$-$C_6$) alkyl; $R_7$ is hydrogen; straight or branched ($C_1$-$C_7$) alkyl; —($CH_2$)$_n$-cyclic ($C_3$-$C_7$ )alkyl, n=0-4; or W is —NH—$R_{10}$, —O$R_{10}$ or —NHCH$R_{10}R_{11}$; wherein $R_{10}$ is a straight or branched ($C_1$-$C_8$)alkyl; —($CH_2$)$_n$-cyclic($C_3$-$C_7$)alkyl, n=0-4; —($CH_2$)$_n$-phenyl, n=0-4; —($CH_2$)$_n$-substituted phenyl, n=0-4, substituted with F, Cl, Br, I, ($C_1$-$C_4$)alkoxide, straight, branched or cyclic ($C_1$-$C_6$)alkyl; —($CH_2$)$_n$-heterocycle, n=0-4, and the heterocycle is defined as a stable 5- to 7-membered mono-or bicyclic or a stable 7- to 10-membered bicyclic heterocyclic ring which is either saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and may include any bicyclic group in which any of the above defined heterocycles is fused to a benzene ring; or —($CH_2$)$_n$-substituted heterocycle. n=0-4, substituted with F, Cl, Br, I, ($C_1$-$C_4$)alkoxide, straight, branched or cyclic ($C_1$-$C_6$)alkyl, and the heterocycle is as defined hereinabove; $R_{11}$ is a straight or branched ($C_1$-$C_6$)alkyl optionally substituted with —OH; —($CH_2$)$_n$-cyclic($C_3$-$C_7$)alkyl, n=0-4; —($CH_2$)$_n$-phenyl, n=0-4; —($CH_2$)$_n$-substituted phenyl, n=0-4, substituted with F, Cl, Br, I, ($C_1$-$C_4$)alkoxide, straight, branched or cyclic ($C_1$-$C_6$)alkyl; or —COO$R_{12}$ wherein $R_{12}$ is straight or branched ($C_1$-$C_7$)alkyl; $R_8$ is hydrogen; straight or branched ($C_1$-$C_7$)alkyl; or $R_6$ and $R_7$ taken together may be —($CH_2$)$_2$— or $$A-\overset{|}{\underset{|}{CH}}$$
$$(CH_2)_i \quad (CH_2)_g$$
$$\underset{R_{76}}{\overset{|}{CH}} (CH_2)_h \underset{R_{67}}{\overset{|}{CH}}$$

g, h and i are independently 0–3 provided that g+h+i is less than 4;

$R_{67}$ is hydrogen; straight or branched ($C_1$-$C_4$)alkyl; or straight or branched ($C_1$-$C_4$)alkoxy;

$R_{76}$ is hydrogen; straight or branched ($C_1$-$C_4$)alkyl; or straight or branched ($C_1$-$C_4$)alkoxy;

A is hydrogen or $$R_9U-\overset{O}{\underset{}{\overset{||}{C}}}-\underset{H}{N}-$$

U is a single bond, oxygen or NH;

$R_9$ is a straight or branched ($C_1$-$C_8$)alkyl; —$(CH_2)_n$-cyclic($C_3$-$C_7$)alkyl, n=0–4; —$(CH_2)_n$-phenyl, n=0–4; —$(CH_2)_n$-substituted phenyl, n=0–4, substituted with F, Cl, Br, I, ($C_1$-$C_4$)alkoxide, straight, branched or cyclic ($C_1$-$C_6$)alkyl; —$(CH_2)_n$-1-naphthyl, n=0–4; —$(CH_2)_n$-1-substituted naphthyl, n=0–4, substituted with F, Cl, Br, I, ($C_1$-$C_4$)alkoxide, straight, branched or cyclic ($C_1$-$C_6$)alkyl; —$(CH_2)_n$-2-naphthyl, n=0–4; —$(CH_2)_n$-2-substituted naphthyl, n=0–4, substituted with F, Cl, Br, I, ($C_1$-$C_4$)alkoxide, straight, branched or cyclic ($C_1$-$C_6$)alkyl; —$(CH_2)_n$-2-quinolyl, n=0–4; —$(CH_2)_n$-2-substituted quinolyl, n=0–4, substituted with F, Cl, Br, I, ($C_1$-$C_4$)alkoxide, straight, branched or cyclic ($C_1$-$C_6$)alkyl; —$(CH_2)_n$-heterocycle, n=0–4, and the heterocycle is as defined hereinabove; —$(CH_2)_n$-substituted heterocycle, n=0=4, substituted with F, Cl, Br, I, ($C_1$-$C_6$)alkoxide, straight, branched or cyclic ($C_1$-$C_6$)alkyl, and the heterocycle is as defined hereinabove;

$R_5$ is a moiety of the formula:

$$R_7-\underset{R_8}{\overset{R_6}{\overset{|}{\underset{|}{C}}}}\sim$$

wherein $R_6$, $R_7$ and $R_8$ are as defined hereinabove; and the pharmaceutically acceptable salts thereof, are useful as inhibitors of the function of HIV protease.

DESCRIPTION OF THE PREFERRED EMBODIMENT

Preferred compounds are compounds of formula II:

wherein:

X, Y, Z, $R_1$, $R_5$, $R_6$ and $R_7$ are defined hereinabove.

Also preferred are compounds of formula III:

wherein: X, Y, Z, $R_1$, and $R_9$ are as defined hereinabove and $R_{50}$ is straight or branched ($C_1$-$C_7$) alkyl.

Most particularly preferred are compounds of formula IV:

wherein:

X, Y, Z, $R_1$ and $R_{50}$ are as defined hereinabove, $R_{60}$ is straight or branched ($C_1$-$C_7$)alkyl; —$(CH_2)_n$-cyclic ($C_3$-$C_7$)alkyl, n=0–4; —$(CH_2)_2CONH_2$; —$CH_2CONH_2$; —$CH_2OH$ or —$CH(CH_3)OH$;

$R_{70}$ is $$W_1\sim\underset{O}{\overset{||}{\underset{}{C}}}$$

wherein W1, is —$NH(CH_2)_j$-phenyl, j=0–1; —$NH(CH_2)_j$-substituted phenyl, j=0–1, substituted with F, Cl, Br, I, ($C_1$-$C_4$)alkoxide, straight, branched or cyclic ($C_1$-$C_6$)alkyl; —$NH(CH_2)$j-T, j=0–1, wherein T is selected from piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoazolidinyl, morpholinyl, thiazolyl, thiazolidinyl, isothiazolyl, benzofuranyl, benzodioxanonyl, quinuclidinyl, isothiazolidinyl, indolyl, quinolinyl, isoquinolinyl, benzimidazolyl, thiadiazoyl, benzopyranyl, benzothiapyranyl, benzothiazolyl, benzoxaxolyl, furyl, tet- rahydrofuryl, tetrahydropyranyl, thienyl, benzothienyl, thiamorpholinyl, thiamorpholinyl sulfoxide, thiamorphoiinyl sulfone and oxadiazolyl; or —NH(CH$_2$)$_j$-substituted T, j=0-1, T is defined hereinabove, substituted with F, Cl, Br, I, (C$_1$-C$_4$)alkoxide, straight, branched or cyclic (C$_1$-C$_6$)alkyl.

Also included in the present invention are compounds useful as intermediates for producing the compounds of the present invention. Such intermediate compounds include those of the formula V:

wherein: a, b, c, Z, R$_1$, R$_2$, R$_4$ and R$_5$ are as defined hereinabove.

Additional intermediates for producing the compounds of the present invention include those of the formula VI:

wherein: a, b, c, Z, R$_1$, R$_2$, R$_3$, R$_4$ and R$_5$ are as defined hereinabove and PP is CH$_2$ or O.

Additional intermediates for producing the above compounds include those of the formula VII:

wherein: a, b, c, Z, R$_1$, R$_2$, R$_4$ and R$_5$ are as defined hereinabove.

Novel methods of making the compounds described above are also provided as are novel methods of using the compounds in the inhibition of HIV protease enzyme and pharmaceutical compositions containing the compounds.

The retroviral protease inhibiting compounds of the present invention are prepared as follows. An important intermediate in the preparation of the compounds of this invention are compounds of the formula VII.

Compounds of formula VII, wherein R$_1$, R$_2$, R$_4$, Z, a, b, and c are hereinabove defined, are prepared as described below. Commercially available 3-chloro-2-chloromethyl-1-propene is converted into diiodide 102 upon treatment with sodium iodide in acetone.

Commercially available (S)-(—)-4-benzyl-2-oxazolidinone is converted into substituted oxazolidinones of formula 103 upon treatment with base and acid chlorides of the formula R$_1$CH$_2$COCl, wherein R$_1$ is hereinabove defined, following the methodology of Evans et al., (J.Am. Chem. Soc., 104, 1737-9(1982)).

Other oxazolidinones of the general formula:

in which D=(C$_1$-C$_7$)alkyl; —(CH$_2$)$_n$-phenyl, n=0-4; E and F are the same or different and are selected from H, (C$_1$-C$_7$)alkyl and —(CH$_2$)$_n$-phenyl, n=0-4, are equally effective as alternatives to 103. When D is —(CH$_2$)$_n$-phenyl, E and F are hydrogen and n=1, the compound of formula 103 results.

The anion of 103 is prepared by treatment of 103 with strong base, eq NaN(TMS)$_2$, in which TMS=trimethylsilyl, at temperature <—70° C. When an excess of compound 102 is allowed to react with the anion of 103 at low temperatures, a compound of formula 104 is produced.

When compounds of formula 104 are allowed to react with secondary amines of formula 105, in the presence of a tertiary amine base such as N,N-diisopropylethylamine, compounds of formula V are formed. Treatment of compounds of formula V with hydrogen peroxide and lithium hydroxide produce acids of formula VII. The chemistry used to prepare compounds of formula VII is compatible with a wide variety of R$_1$, R$_2$, R$_4$ and R$_5$ groups.

When compounds of formula VII are allowed to react with amines of formula R$_3$NH$_2$ where R$_3$ is defined hereinabove in the presence of BOP, a tertiary amine such as N,N-diisopropylethylamine and optionally HOBT, compounds of formula 107 are produced, where BOP=benzotriazol-1-yloxytris(dimethylamino)phosphoniumhexafluorophosphate and HOBT=1-hydroxybenzotriazole.

Other methods for formation of amide bonds, including DCC mediated coupling, are applicable, where DCC=1,3-dicyclohexylcarbodiimide. A wide variety of $R_3$ groups are compatible with the above chemistry.

Compounds of formula 107, are converted into their corresponding diols 108, upon treatment with osmium tetraoxide in the presence of pyridine.

Diols of formula 108, upon treatment with sodium periodate, are converted into intermediate ketones 109, which are reduced upon treatment with sodium borohydride to give alcohols 110.

Pharmaceutically suitable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hygroscopiticity and solubility. Preferred salts of this invention for the reasons cited above include the inorganic salts: hydrochloric, hydrobromic, hydroiodic, phosphoric, nitric or sulfuric; as well as organic salts: acetate or other alkylcarboxylates, benzoate or other arylcarboxylates, citrate, cysteine or other amino acids, fumarate, glycolate, maleate, succinate, tartrate, alkylsulfonate, arylsulfonate, trifluoroacetate or trifluoromethanesulfonate.

BIOLOGICAL ACTIVITY

IC$_{50}$ values for enzyme inhibition are determined using HIV-1 and Amersham's HIV proteinase [$^{125}$I]-scintillation proximity assay (SPA). The results are given in Table 1.

Amersham's HIV proteinase [$^{125}$I]-SPA system is a commercial assay incorporating the scintillation proximity assay (SPA) principle available from Amersham International PLC, Bucks, England.

The SPA microspheres provided by Amersham have the substrate linked directly to the surface through a streptavidin-biotin link. The substrate is a 12 residue peptide designed specifically for this application utilizing current knowledge of known cleavage sites for the enzyme and analogue substrate studies. The sequence of the substrate is:

The peptide is monoiodinated on the tyrosine residue and biotinylated through the epsilon-NH$_2$ group on the lysine. It is linked to the SPA bead via a streptavidin-link. The beads are suspended in a buffer consisting of 5 mM DTT, 1 mM EDTA, 10% w/v glycerol, 0.05% W/v sodium azide, 0.01% v/v Triton X-100 in 25 mM sodium citrate buffer pH 5.5.

The enzyme cleaves at the Phe-Phe bond releasing the $^{125}$I fragment from the bead. This event causes the removal of detectable signal from the microsphere. Once the peptide fragment has left the bead it can no longer stimulate the scintillant and the signal therefore is reduced. The rate of reduction in signal is proportional to the activity of the enzyme. The obtained data is used to calculate the IC$_{50}$ values found in Table 1.

TABLE 1

| Activity of Compounds as Enzyme Inhibitor | |
|---|---|
| Compound from Example # | IC$_{50}$ (µg/ml) |
| 21 | 0.05 |

TABLE 1-continued

| Activity of Compounds as Enzyme Inhibitor | |
|---|---|
| Compound from Example # | IC$_{50}$ (μg/ml) |
| 23 | 0.05 |
| 24A | 0.05 |
| 24B | 0.05 |
| 26 | 0.50 |
| 28 | 0.10 |
| 30 | 0.25 |
| 32 | 0.50 |
| 35 | 0.05 |
| 37 | 0.05 |
| 40 | 0.04 |
| 42 | 0.055 |
| 51 | 0.09 |

In Table 2, data is shown for the ability of these compounds to inhibit growth of HIV-1 strain IIIB in T lymphoid MT-2 cell lines. The cell line is challenged by free virons selected to result in 90–95% cell death (CPE) by day 5. The protease inhibitor compound is then added in the stated concentration. After 5 days, the surviving cells are measured using metabolic MTT dye.

TABLE 2

| Activity of Compounds as Antiviral | | | | | |
|---|---|---|---|---|---|
| Compound from | % Inhibition at concentration (μg/ml) | | | | |
| Example # | 2.5 | 0.625 | 0.156 | 0.039 | 0.010 |
| 21 | 102.4 | 102.9 | 33.0 | 8.1 | 0 |
| 23 | 98.5 | 95.8 | 93.6 | 78.7 | 13.0 |
| 24A | 96.0 | 102.6 | 100.1 | 63.3 | 10.7 |
| 24B | 94.9 | 94.7 | 93.0 | 81.4 | 16.2 |
| 35 | 0.00 | 0.00 | 1.97 | 0.00 | 0.0 |
| 37 | 49.15 | 4.37 | 0.00 | 0.00 | 0.95 |
| 40 | 13.79 | 0.91 | 1.88 | 0.00 | 0.0 |
| 42 | 86.75 | 12.91 | 4.21 | 0.00 | 4.33 |
| 51 | 72.91 | 55.08 | 10.44 | 2.24 | 1.67 |

As can be seen from the data presented hereinabove in Table 1 and 2, the compounds of the present invention are potent inhibitors of the HIV-1 protease enzyme and thus are useful in treating mammals infected with retroviruses, especially HIV-1. The present invention also includes combinations of the HIV protease inhibitory compounds with one or more other agents useful in the treatment of AIDS.

When the compounds are employed for the above utility, they can be combined with one or more pharmaceutically acceptable carriers, for example, solvents, diluents and the like, and may be administered orally in such form as tablets, capsules, dispersible powders, granules, or suspensions containing, for example, from about 0.05 to 5% of suspending agent, syrups containing, for example, from about 10 to 50% of sugar and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

An effective amount of compound from 0.2 mg/kg of body weight to 100.0 mg/kg of body weight should be administered one to five times per day via any topical route of administration including but not limited to oral, parenteral (including subcutaneous, intravenous, intramuscular, intrasternal injection or infusion techniques), by inhalation spray, or rectally, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

These active compounds may be administered orally as well as by intravenous, intramuscular, or subcutaneous routes. Solid carriers include starch, latose, dicalcium phosphate, microcrystalline celulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitble mixtures thereof, and vegetable oil.

Figure 1:
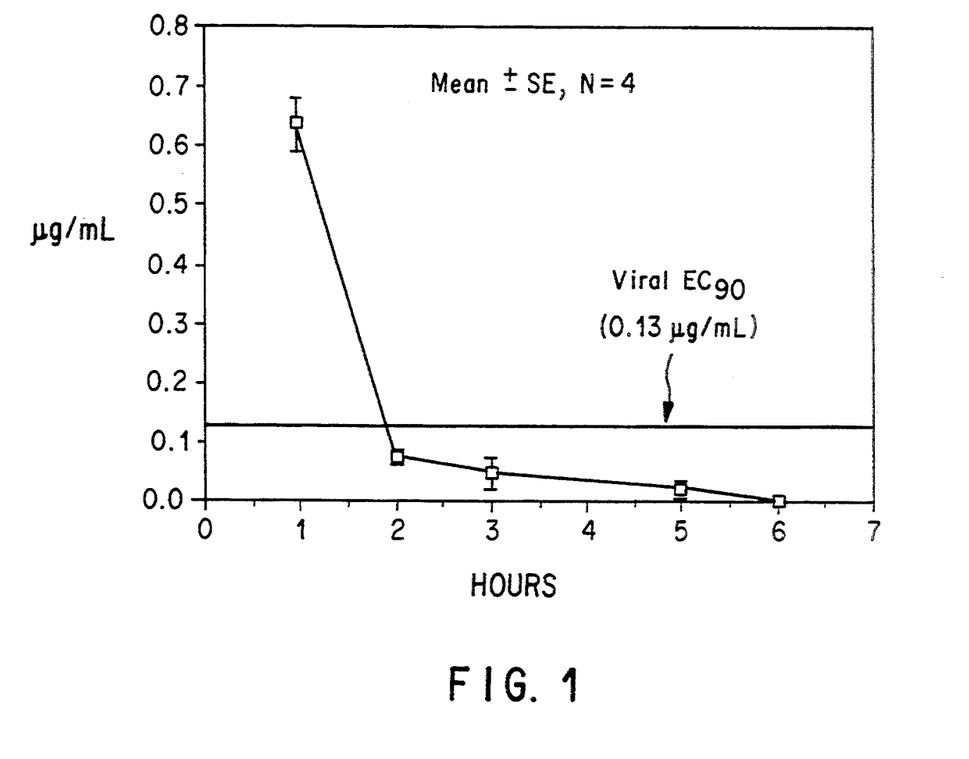
FIG. 1 depicts the mouse plasma level of the compound of Example 24B after oral (16.6 mg/kg) administration.

For [3S-[2[alphaS*(1R*,2R*),gammas*(or R*)], 3alpha,4abeta,8abeta]]-N-[1-[[(1H-benzimidazol-2-ylmeth-yl)amino]carbonyl]-2-methylbutyl]-3-[[(1,1-dimethylethyl)amino]carbonyl]decahydro-gamma-hydroxy-alpha-(ph-enylmethyl)-2-isoquinolinepentanamide, Example 24B, in an aqueous liposomal formulation, concentrations of >0.13 microgram/ml in plasma are achieved in mice for 2.8 and 4.2 hours following IP injection with doses of 8.3 and 16.6 mg/kg respectively. Concentrations >0.13 microgram/ml of Example 24B in plasma are also maintained for 2 hours following oral administration of a dose of 16.6 mg/kg (FIG. 1). Such a concentration (>0.13 microgram/ml) results in a >90% inhibition of HIV-1 strain IIIB viral growth in MT-2 cell lines (Table 2). A suitable aqueous liposomal formulation comprises Egg phosphatidyl glycerol, dimyristoyl phosphatidyl choline, butylated hydroxy toluene, lactose and water.

The invention will be more fully described in conjuction with the following specific examples which are not to be construed as limiting the scope of the invention.

EXAMPLE 1

[S-(R*,R*)]-[2-Methyl-1-[[(2-pyridinylmethyl)amino]-carbonyl]butyl]carbamic acid 1,1-dimethethyl ester To a room temperature solution of 2.33 g of N-(tert-butoxycarbonyl)-L-isoleucine in 5 ml of methylene chloride is added, in the following order, 1.0 g of 2-(aminomethyl)pyridine in 5 ml of methylene chloride, 6.95 g of BOP in 5 ml of methylene chloride and 16 ml of Hunig's base. The reaction is stirred at room temperature for 2 hours, diluted with methylene chloride, and, washed with saturated sodium chloride. The organic layer is dried, filtered and concentrated in vacuo. Purification by chromatography (400 g Silica Gel; 90% ethyl acetate/hexane) gives 3.03 g of the desired product as an oil.

MS (FAB): m/z 322 (M+H).
$[\alpha]_D^{26}$ −31±1.

EXAMPLE 2

[S-(R*,R*)]-2-Amino-3-methyl-N-(2-pyridinylmethyl)-pentanamide trifluoroacetate

To 2.35 g of product from Example 1 in 10 ml of methylene chloride is added 2.8 ml of trifluoroacetic acid. The reaction is heated at 80°–90° C. for 4½ hours and then concentrated in vacuo to give 3.6 g of the desired product as tris-trifluoroacetic acid salt.

MS (FAB): m/z 222 (M+H).
$[\alpha]D^{26}$ = −36±1.

EXAMPLE 3

[S-(R*,R*)]-[2-Methyl-1-[[(3-pyridinylmethyl)amino]-carbonyl]butyl]carbamic acid 1,1-dimethylethyl ester The title compound is prepared by the procedure of Example 1, using 1.0 g of 3-(aminomethyl)pyridine, 2.33 g of N-(tert-butoxycarbonyl)-L-isoleucine, 6.95 g of BOP, 11.95 g of Hunig's base and 15 ml of methylene chloride to give 2.1 g of the desired product after chromatography.

MS (FAB): m/z 322 (M+H).
$[\alpha]_D^{26}$ = −9±1.

EXAMPLE 4

[S-(R*,R*)]-2-Amino-3-methyl-N-(3-pyridinylmethyl)-pentanamide trifluoroacetate

The title compound is prepared by the procedure of Example 2, using 2.0 g of product from Example 3 and 3.55 g of trifluoroacetic acid to give 3.6 g of the desired product as a tacky oil.

MS(FAB): m/z 222 (M+H).

EXAMPLE 5

[S-(R*,R*)]-[2-Methyl-1-[[[2-(2-pyridinyl)ethyl]amino]-carbonyl]butyl]carbamic acid 1,1-dimethylethyl ester The title compound is prepared by the procedure of Example 1, using 1.0 g of 2-(2-amino-ethyl)pyridine, 2.163 g of N-(tert-butoxycarbonyl)-L-isoleucine, 6.15 g of BOP, 10.52 g of Hunig's base, and 15 ml of methylene chloride to give 2.5 g of the product as a white/yellow powder.

MS (FAB): m/z 336 (M+H).
$[\alpha]_D^{26}$ = −11±1.

EXAMPLE 6

[S-(R*,R*)]-2-Amino-3-methyl-N-[2(2-pyridinyl)ethyl]-pentanamide trifluoroacetate The title compound is prepared by the procedure of Example 2 using 2.33 g of product from Example 5 and 2.6 ml of trifluoroacetic acid to give 3.7 g of the desired product.

MS (FAB): m/z 236 (M+H).
$[\alpha]_D^{26}$ = +23±1.

EXAMPLE 7

N-L-Leucyl-L-leucine methyl ester

To 0.50 g of L-leucine-L-leucine, under argon, is added, via a syringe, 10 ml of methyl alcohol and 0.610 ml of trimethylsilyl chloride. The reaction is stirred overnight at room temperature. The mixture is concentrated in vacuo to give 0.554 g of the desired product.

MS (FAB): m/z 259 (M+H).
$[\alpha]_D^{26}$ = −10±2.

EXAMPLE 8

N-L-leucyl-L-phenylalanine methyl ester

The title compound is prepared by the procedure of Example 7 using 0.50 g of L-leucine-L-phenylalanine, 10 ml of methyl alcohol and 0.536 ml of trimethylsilyl chloride to give 0.53 g of the desired product.

MS (FAB): m/z 293 (M+H).
$[\alpha]D^{26}$ = +10±1.

EXAMPLE 9

N-L-Valyl-L-phenylalanine methyl ester

The title compound is prepared by the procedure of Example 7 using 0.50 g of L-valine-L-phenylalanine, 10 ml of methyl alcohol and 0.564 ml of trimethylsilyl chloride to give 0.57 g of the desired product.

MS (FAB): m/z 279 (M+H).
$[\alpha]_D^{26}$ = ±29±2.

EXAMPLE 10

N-L-Valyl-L-valine methyl ester

The title compound is prepared by the procedure of Example 7 using 0.50 g of L-valine-L-valine, 10 ml of methyl alcohol and 0.689 ml of trimethylsilyl chloride to give 0,657 g of the desired product.

MS(FAB): m/z 231 (M+H).
$[\alpha]_D^{26}$ = +5±1.

EXAMPLE 11

[S-(R*,R*)]-[1-[[(1H-Benzimidazol-2-ylmethyl)amino]-carbonyl]-2-methylbutyl]carbamic acid 1,1-dimethylethyl ester The title compound is prepared by the procedure of Example 1 using 0.505 g of N-(tert-butoxycarbonyl)-L-isoleucine in 10 ml of methylene chloride, 0.500 g of 2-(aminomethyl)benzimidazole dihydrochloride hydrate, 1.07 g of BOP, and 0,850 g of triethylamine. Purification by chromatography (75 g Silica gel; 70% ethyl acetate/hexane) gives 0.669 g of the desired product.

MS(EI): m/z 360 M+.
$[\alpha]_D^{26}$ = −39±1.

EXAMPLE 12

[S-(R*,R*)]-2-Amino-N-(1H-benzimidazol-2-ylmethyl)-3-methylpentanamide tris(trifluoroacetate)

The title compound is prepared by the procedure of Example 2 using 0.588 g of product from Example 11 in 6 ml of methylene chloride and 1.3 g of trifluoroacetic acid (TFA). The resulting desired intermediate is used as is in the next reaction. The $^1$HNMR indicates the correct product with associated TFA molecules.

EXAMPLE 13

[3S-(3alpha,4abeta,8abeta)]-Octahydro-2(1H),3-isoquinolinedicarboxylic acid 1-(phenylmethyl) ester To a 0° C. solution of 3.0 g of [3S-(3alpha,4abeta,8abeta)]-decahydro-3-isoquinolinecarboxylic acid in 75 ml of water is added 3.5 ml of 5M sodium hydroxide. After 15 minutes, 6.15 g of benzyl chloroformate is added. During the addition the pH is maintained at >10 with sodium hydroxide. The reaction mixture is stirred at 0° C. for 2 hours, made acidic (pH 2) with 10% hydrochloric acid and extracted with methylene chloride. The organic layer is washed with saturated sodium chloride, dried, filtered and concentrated in vacuo. The residue is purified twice by chromatography (250 g Silica Gel; gradient elution 0–20% methanol/chloroform) to give 2.0 g of the desired product.

MS(EI): m/z 317 (M+).

EXAMPLE 14

[3S-(3alpha,4abeta,8abeta)]-3-[[(1,1-Dimethylethyl)amino]carbonyl]octahydro-2(1H)-isoquinolinecarboxylic acid phenylmethyl ester To a room temperature solution of 0.050 g of product from Example 13 in 2 ml of methylene chloride is added 0.090 g of BOP, 0.015 g of t-butylamine and 0.159 g of triethylamine, The reaction is stirred at room temperature for 5 hours, poured into a solution of half saturated sodium chloride, and extracted with methylene chloride, The organic layer is washed with saturated sodium chloride, dried, filtered and concentrated in vacuo, The residue is purified by chromatography (silica Gel; 20% ethyl acetate/hexane) to give 0.046 g of product as a colorless oil, MS(EI): m/z 372 M+.

EXAMPLE 15

[3S(3alpha,4abeta,8abeta)]-N-(1,1-Dimethylethyl)-decahydro-3-isoquinolinecarboxamide To a solution of 0.045 g of product from Example 14 in 1 ml of ethyl alcohol is added 0.010 g of 10% Pd/C and the reaction vessel is fitted with a balloon filled with hydrogen. The reaction is stirred at room temperature for 3 hours, filtered and concentrated in vacuo. The residue is purified by chromatography (Silica Gel; 10% methyl alcohol/chloro- form) to give 0.0175 g of product as a colorless oil.

An alternative 1 step process for making [3S-(3alpha,4abeta,8abeta)]-N-(1,1-dimethylethyl)decahydro-3-isoquinolinecarboxamide is as follows:

To a 0° C. solution of 2.0 g of [3S-(3alpha,4abeta,8abeta)]-decahydro-3-isoquinolinecarboxylic acid in 40 ml of methylene chloride is added 39.91 g of t-butylamine, ! 4.11 g of Hunig's base, and 6.28 g of BOP in 20 ml of methylene chloride. The reaction is stirred at 0° C. for 1 hour followed by 3 hours at room temperature. The mixture is poured in saturated sodium chloride and extracted with methylene chloride. The organic layer is washed with saturated sodium chloride, dried, filtered and concentrated in vacuo. The residue is purified by chromatography (155 g Silica Gel; 10% methyl alcohol/chloroform) to give 3.1 g of the desired product as a tan foam.

$^1$H NMR(CDCl$_3$):d 6.65(s,1H); 3.1(m, 1H); 2.8(brs,2H); 2.45(brs,1H); 1.85–1.25(m,12H); 1.3(s,9H).

EXAMPLE 16

(S)-2-Oxo-3-(1-oxo-3-phenylpropyl)-4-(phenylmethyl)-2-oxazolidinone

To a −78° C. solution of 25 g of (S)-(−)-4-benzyl-2-oxazolidinone in 375 ml of dry tetrahydrofuran is added, dropwise, 57 ml of 2.5M n-butyllithium. The mixture is stirred at −78° C. for 15 minutes, 22 ml of hydrocinnamoyl chloride is added and the solution warmed to room temperature. The reaction is quenched with water, extracted with ethyl acetate, dried and concentrated in vacuo. The residue is recrystallized from ethyl acetate/hexane to give 38 g of the desired product.

MP 92°–93° C.

$^1$H NMR(CDCL$_3$):d 2.75(dd, 1H); 3.03(m,2H); 3.21–3.33(m,3H); 4.16(m,2H); 4.65(m, 1H) ;7.15–7.35(m,10H).

EXAMPLE 17

(4S)-3-[4-(Iodomethyl)-1-oxo-2-(phenylmethyl)-4-pentenyl]-4-(phenylmethyl)-2-oxazolidinone To a −78° C. solution of 7.43 ml of 1M sodium bis(trimethylsilyl)amide is added a solution of 2.0 g of the product of Example 16 dissolved in 10 ml of dry tetrahydrofuran dropwise. Five minutes later, 3.98 g of 3-iodo-2-iodo-methyl-1-propene in 5 ml of dry tetrahydrofuran is added, dropwise. The reaction is stirred at −78° C. for 2 hours followed by warming to room temperature and quenching with saturated ammonium chloride. The residue is purified by chromatography to give 2.3 g of the desired product.

$[\alpha]_D^{26}=+92\pm1$.

MS (FAB): m/z 490 (M+H).

EXAMPLE 18

[3S-[2[R*,R*)]3alpha,4abeta,8abeta]-N-(1,1-Dimethylethyl)decahydro-2-[2-methylene-5-oxo-5-[2-oxo-4-(phenylmethyl)-3-oxazolidinyl]-4-(phenylmethyl)pentyl]-3-isoquinolinecarboxamide A mixture of 5.91 g of product from Example 17, 2.4 g of product from Example 15, 3.9 g of Hunig's base and 50 ml of toluene is heated in an oil bath at 100° C. for 2.5 hours. The reaction is cooled to room temperature, diluted with saturated sodium bicarbonate, and extracted with methylene chloride. The organic layer is washed with saturated sodium chloride, dried, filtered and concentrated in vacuo to give 10.5 g of crude product. The residue is purified by chromatography (650 g Silica Gel; 20–35% ethyl acetate/hexane) to give 4.83 g of product as a yellow foam.

$[\alpha]_D^{26}=+19\pm2$.

EXAMPLE 19

[3S-[2(R*),3alpha,4abeta,8abeta]]-3-[[(1,1-Dimethylethyl)amino]carbonyl]decahydro-gamma-methylene-alpha-(phenylmethyl)-2-isoquinolinepentanoic acid To a 0° C. solution of 0.20 g of product from Example 18 dissolved in 4 ml of tetrahydrofuran and 1 ml of water is added 0.028 g of lithium hydroxide monohydrate and 0.08 ml of 30% hydrogen peroxide. The reaction is stirred at 0° C. for 4¾ hours and then poured into a 0° C. solution of 0.215 g sodium sulfite dissolved in 10 ml of water. The reaction is stirred for 5 minutes and the pH is adjusted to 7 with 10 % hydrochloric acid. The reaction is extracted with methylene chloride. The combined organic extracts are washed with saturated sodium chloride, dried, filtered and concentrated in vacuo to give 0.205 g of the desired product as a thick yellow oil. The product is used as is in the next reaction.

$^1$H NMR(CDCl$_3$):d 7.3–7.15(m,5H); 5.35(s,1H); 5.3(s,1H); 4.15(brs,1H); 3.65(brs,1H); 3.05–0.65(m,30 H).

EXAMPLE 20

[3S-[2[alphaR*(1R*,2R*)],3R*,4abeta,8abeta]]-N-[1-[[(1H-Benzimidazol-2-ylmethyl)amino]carbonyl]-2-methylbutyl]-3-[[(1,1-dimethylethyl)amino]carbonyl]-decahydrogamma-methylene-alpha(phenylmethyl)-2-isoquinolinepentanamide To 0.149 g of product from Example 19 dissolved in 10 ml of methylene chloride is added 0.407 g of product from Example 12, 0.224 g of BOP and 0.874 g of Hunig's base. The reaction is stirred at room temperature for 5.5 hours, poured into 75 ml of half saturated sodium chloride and extracted with methylene chloride. The organic layer is washed with saturated sodium chloride, dried, filtered and concentrated in vacuo to give 0.60 g of crude product. The residue is purified by chromatography (50 g Silica Gel; ethyl acetate) to give 0.190 g of product as a yellow oil/foam.

MS (FAB): m/z 683 (M+H).

EXAMPLE 21

[3S-[2[alphaS*(1R*,2R*),gammaR*(and S*),3alpha,4abeta,8abeta]]-N[1-[[(1H-Benzimidazol-2-ylmethyl)amino]carbonyl]-2-methylbutyl]-3-[[(1,1-dimethylethyl)amino]carbonyl]decahydro-gamma-hydroxy-gamma-(hydroxymethyl)alpha-(phenylmethyl)-2-isoquinolinepentanamide To 0.225 g of product from Example 20 dissolved in 10 ml of toluene and 1.33 ml of pyridine is added, in one portion, 0.1256 g of osmium tetroxide. The reaction is stirred at room temperature, in the dark, for 1.5 hours, followed by concentration in vacuo. The residue is dissolved in methyl alcohol/water (9/1), 0.750 g of sodium bisulfite is added and the reaction is stirred for 45 minutes. The mixture is poured into saturated sodium chloride and extracted with methylene chloride. The organic extracts are washed with saturated sodium chloride, dried, filtered and concentrated in vacuo. The residue is purified by chromatography (2×, 70 g Silica Gel, 5% methyl alcohol/chloroform) to give 0.214 g of crystalline product.

MS (FAB): m/z 717 (M+H).

EXAMPLE 22

[3-[2[alphaS*(1R*,2R*)]3alpha,4abeta,8abeta]]-N-[1-[[(1H-Benzimidazol-2-ylmethyl)amino]carbonyl]-2-methylbutyl]-3-[[(1,1-dimethylethyl)amino]carbonyl]decahydro-gamma-oxo-alpha-(phenylmethyl)-2-isoquinolinepentanamide To 0.190 g of product from Example 21 in 8 ml of tetrahydrofuran and 2 ml of water is added 0.113 g of sodium periodate. The reaction is stirred at room temperature for 2.5 hours. The mixture is diluted with saturated sodium chloride and extracted with methylene chloride. The organic layers are washed with saturated sodium chloride, dried, filtered, and concentrated in vacuo. The residue is partially purified by chromatography (10 g Silica Gel; 5% methyl alcohol/chloroform) to give 0.160 g of the desired product. The product is used as is in the next reaction.

MS (FAB): m/z 685 (M+H).

EXAMPLE 23

[3S-[2[alphaS*(1R*,2R*),gammaR* (and S*)],3alpha,4abeta,8abeta]]-N-[1-[[(1H-Benzimidazol-2-ylmethyl)amino]carbonyl]-2-methylbutyl]-3-[[(1,1-dimethylethyl)amino]carbonyl]decahydro-gamma-hydroxy-alpha-(phenylmethyl)-2-isoquinolinepentanamide To 0.16 g of product from Example 22 in 10 ml of ethyl alcohol is added 0.0884 g of sodium borohydride. The reaction is stirred at room temperature for 1 hour, diluted with saturated sodium chloride and extracted with methylene chloride. The organic extracts are washed with saturated sodium chloride, dried, filtered and concentrated in vacuo. The residue is purified by chromatography (2×, 50 g Silica Gel; 7% methyl alcohol/chloroform) to give 0.140 g of a mixture of 2 diastereoisomers.

MS (FAB): m/z 687 (M+H).

EXAMPLE 24

[3S-[2[alphaS*(1R*,2R*),gammaR*(or S*),3alpha,4abeta,8abeta]]-N-[1-[[(1H-Benzimidazol-2-ylmethyl)amino]carbonyl]-2-methylbutyl]-3-[(1,1-dimethylethyl)amino]carbonyl]decahydro-gamma-hydroxy-alpha-(pentylmethyl)-2-isoquinolinepentanamide (A)

and

[3S-[2[alphaS*(1R*,2R*),gammaS*(or R*)],3alpha,4abeta,8abeta]]-N-[1-[[(1H-Benzimidazol-2-ylmethyl)amino]carbonyl]-2-methylbutyl]-3-[[(1,1-dimethylethyl)amino]carbonyl]decahydro-gamma-hydroxy-alpha-(phenylmethyl)-2-isoquinolinepentanamide (B)

The above mixture of 2 diastereoisomers, product of Example 23, is purified by chromatography (2000 micron preparative Silica Gel plates, 9/0.5–9/1 chloroform/methyl alcohol) to give 0.0107 g of the more polar isomer (A) and 0.0692 g of the less polar isomer(B).

MS(FAB): m/z 687 (M+H) for both isomers.

EXAMPLE 25

[3S-[2R*[1R*,1(R*)]3alpha,4abeta,8abeta]]-3-[[(1,1-Dimethylethyl)amino]carbonyl]octahydro-gamma-methylene-N-[2-methyl-1-[[(2-pyridinylmethyl)amino]carbonyl]butyl]-alpha-(phenylmethyl)-2(1H)-isoquinolinepentanamide The title compound is prepared by the procedure of Example 1 using 0.070 g of product from Example 19, 0.107 g of product from Example 2, 0.091 g of BOP, 0.205 g of Hunig's base and 4 ml of methylene chloride to give 0.099 g of the desired product after chromatography.

MS(FAB): m/z 644 (M+H).

EXAMPLE 26

[3S-[2[gammaR*(and S*),gamma[alphaS*[1R*,1(R*)]]],3alpha,4abeta,8abeta]]-3-[[(1,1-Dimethylethyl)amino]carbonyl]octahydro-gamma-hydroxy-gamma-(hydroxymethyl)-N-[[2-methyl-1-[[(2-pyridinylmethyl)amino]carbonyl]butyl]-alpha-(phenylmethyl)-2(1H)-isoquinolinepentanamide The title compound is prepared by the procedure of Example 21 using 0.099 g of product from Example 25, 0.0586 g of osmium tetroxide, 0.608 g of pyridine and 4 ml of toluene to give 0.085 g of the desired product after chromatography.

MS(FAB): m/z 678 (M+H).

EXAMPLE 27

[3S-[alphaS*[1R*,1(R*)]],3alpha,4abeta,8abeta]]-3-[[(1,1-Dimethylethyl)amino]carbonyl]octahydro-N-[2-methyl-[[(2-pyridinylmethyl)amino]carbonyl]butyl-gamma-oxo-alpha-(phenylmethyl)-2(1H)-isoquinolinepentanamide The title compound is prepared by the procedure of Example 22 using 0.082 g of product from Example 26, 0.0527 g of sodium periodate and 3 ml of tetrahydrofuran/water (2:1) to give 0.053 g of the desired product after chromatography.

MS ( FAB ): m/z 646 (M+H).

EXAMPLE 28

[3S-[2[gammaR*(and S*),gamma[alphaS*[1R,1(R*)]]]],3alpha,4abeta,8abeta]]-3-[[(1,1-Dimethylethyl)amino]carbonyl]octahydro-gamma-hydroxy-N-[2-methyl-1-[[(2-pyridinylmethyl)amino]carbonyl]butyl]-alpha-(phenylmethyl)-2(1H)-isoqinolinepentanamide The title compound is prepared by the procedure of Example 23 using 0.050 g of the product from Example 27, 0.0293 g of sodium borohydride and 3 ml of ethyl alcohol to give 0.0397 g of the desired product after chromatography.

MS (FAB): m/z 648 (M+H).

EXAMPLE 29

[3S-[2(R*),3alpha,4abeta,8abeta]-N-[4-[[3-[[(1,1-Dimethylethyl)amino]carbonyl]octahydro-2(1H)-isoquinolinyl]methyl]-1-oxo-2-(phenylmethyl)-4-pentenyl]-L-isoleucine methyl ester The title compound is prepared by the procedure of Example 1 using 0.070 g of product from Example 19, 0.03175 g of L-isoleucine methyl ester, 0.0913 g of BOP, 0.2053 g of Hunig's base and 4 ml of methylene chloride to give 0.059 g of the desired product after chromatography.

MS (FAB): m/z 568 (M+H).

EXAMPLE 30

3S-[2(2S*),3alpha,4abeta,8abeta]]-N-[5-[3-[[(1,1-Dimethylethyl)amino]carbonyl]octahydro-2(1H)-isoquinolinyl]4-hydroxy-4-(hydroxymethyl)-1-oxo-2-(phenylmethyl)pentyl]-L-isoleucine methyl ester The title compound is prepared by the procedure of Example 21 using 0.055 g of product from Example 29, 0.0369 g of osmium tetroxide, 0.3831 g of pyridine and 2.5 ml of toluene to give 0.0426 g of the desired product after chromatography.

MS(FAB): m/z 602 (M+H).

EXAMPLE 31

[3S-[2(S*),3alpha,4abeta,8abeta]]-N-[5-[3-[[(1,1-Dimethylethyl)amino]carbonyl]octahydro-2(1H)-isoquinolinyl]-1,4-dioxo-2-(phenylmethyl)pentyl]-L-isoleucine methyl ester The title compound is prepared by the procedure of Example 22 using 0.040 g of product from Example 30. 0.02843 g of sodium periodate and 2 ml of tetrahydrofuran/water (1:1) to give 0.043 g of the desired product as a yellow oil.

MS (FAB): m/z 570 (M+H).

EXAMPLE 32

[3S-[2[2S*,4R*(and S*)],3alpha,4abeta,8abeta]-N-[5-[3-[[(1,1-Dimethylethyl)amino]carbonyl]octahydro-2(1H)-isoquinolinyl]-4-hydroxy-1-oxo-2-(phenylmethyl)pentyl]-L-isoleucine methyl ester The title compound is prepared by the procedure of Example 23 using 0.039 g of product from Example 31, 0.0259 g of sodium borohydride and 2 ml of ethyl alcohol to give 0.036 g of the desired product after chromatography.

MS (FAB): m/z 572 (M+H).

EXAMPLE 33

[S-[R*,R*]]-N-(2-Aminocyclohexyl)-2-quinolinecarboxamide

A mixture of 1.0 g of 1,2-diaminocyclohexane, 0.520 g of quinaldic acid, 1.77 g of BOP, 1 ml of triethylamine and 15 ml of methylene chloride is stirred at room temperature for 1 hour. The reaction is quenched with saturated sodium chloride, extracted with ethyl acetate and the organic layer washed with water and saturated sodium chloride. The organic layer is dried, concentrated to dryness and purified by chromatography to give 0.955 g of the desired product.

$^1$H NMR(CDCL$_3$) :d 8.07(d,1H); 8.05(s,2H); 7.95(d,1H); 7.77(t,1H); 7.61(t,1H); 3.82(m, 1H); 3.03(s,2H); 2.82(s,1H); 2.72(m, 1H); 2.08(m,2H); 1.78(m,2H); 1.20–1.50(m,4H).

EXAMPLE 34

[3S-[2[[2R*(2R*,1R*)],3alpha,4abeta,8abeta]]-N-[2-[[4-[[3-[[(1,1-Dimethylethyl)amino]carbonyl]octahydro-2(1H)-isoquinolinyl]methyl]-1-oxo-2-phenylmethyl)-4-pentenyl]amino]cyclohexyl]-2-quinolinecarboxamide The title compound is prepared by the procedures of Example 19 and 20. Following Example 19:0.075 g of product from Example 18, 0.011 g of lithium hydroxide monohydrate, 0.03 ml of 30% hydrogen peroxide, 3 ml of tetrahydrofuran, 0.0095 g of sodium sulfite and 1 ml of water are reacted to give the desired intermediate (A). Following Example 20: intermediate (A) is treated with 0.216 g of product from Example 33, 0.354 g of BOP, 1 ml of triethylamine and 15 ml of methylene chloride to give, after chromatography, 0.070 g of ° the desired product.

$^1$H NMR(CDCL$_3$) :d 8.27(d,1H); 8.2i(d,1H); 8.15(d,1H); 7.88(d, 1H); 7.8(t,1H); 7.43(t,1H); 7.25(m,2H); 6.93(d,2H); 6.75(t,2H); 6.48(t,2H); 5.07(s,1H); 4.88(s,1H); 3.85(m,1H); 3.72(m, 1H); 3.04(d,1H); 1.05–2.82(m,29H); 1.32(s,9H).

EXAMPLE 35

[3S-[2[2S*(2R*,1R*)],3alpha,4abeta,8abeta]]-N-2-[[5-[3-[[(1,1-dimethylethyl)amino]carbonyl]octahydro-2(1H)-isoquinolinyl]-4-(hydroxymethyl)-1-oxo-2-(phenylmethyl)pentyl-]amino]cyclohexyl]-2-quinolinecarboxamide The title compound is prepared by the procedure of Example 21 using 0.015 g of product from Example 34, 0.011 g of osmium tetroxide, 0.1 ml of pyridine, 3 ml of tetrahydrofuran and 0.2 ml of water to give, after chromatography, 0.012 g of the desired product as an oil.

$^1$H NMR(CDCL$_3$):d 8.37(d, 1H); 8.12–8.27(m,3H); 7.85(d, 1H); 7.78(t,1H); 7.62(t,1H); 6.98(m,4H); 6.85(m, 1H); 6.73(d,1H); 5.87(s,1H); 3.90(m, 1H); 3.80(m, 1H); 3.35(d,1H); 3.30(d, 1H): 3.08(d,1H); 1.00–2.70(m,29H); 1.32(s,9H).

MS (FAB): m/z 726 (M+H).

EXAMPLE 36

[3S-[2[2S*(2R*,1R*)],3alpha,4abeta,8abeta]]-N-2-[[5-[3-[[(1,1-dimethylethyl)amino]carbonyl]octahydro-2(1H)-isoquinolinyl]-1,4-dioxo-2-(phenylmethyl)pentyl-]amino]cyclohexyl]-2-quinolinecarboxamide The title compound is prepared by the procedure of Example 22 using 0.0065 g of product from Example 35, 0.010 g of sodium periodate, 1 ml of tetrahydrofuran and 0.2 ml of water to give, after chromatography, 0.0042 g of the desired product as a colorless oil.

$^1$H NMR(CDCL$_3$):d 8.37(d,1H); 8.22(s,2H); 8.15(d,1H); 7.84(d,1H); 7.78(t,1H); 7.62(t,1H); 6.95(m,5H); 6.48(s,1H); 6.38(d,1H); 3.93(m, 1H); 3.78(m, 1H); d,1H); 2.50(3.05(m,5H); 2.27(dd,1H); 1.10–2.20(m,23H); 1.33(s,9H).

EXAMPLE 37

[3S-[2[2S*(2R*,1R*)],3alpha,4abeta,8abeta]]-N-2-[[5-[3-[[(1,1-dimethylethyl)amino]carbonyl]octahydro-2(1H)-isoquinolinyl]-4-hydroxy-1-oxo-2-(phenylmethyl)pentyl]amino]cyclohexyl]-2-quinolinecarboxamide The title compound is prepared by the procedure of Example 23 using 0.011 g of product from Example 36, 0.020 g of sodium borohydride, 2 ml of tetrahydrofuran and 1 ml of methyl alcohol to give, after chromatography, 0.0052 g of the desired product.

$^1$H NMR(CDCL$_3$):d 8.41(d, 1H): 8.37 (d,1H); 8.25(d,1H); 8.17(d,1H); 7.89(d,1H); 7.79(d, 1H); 7.63(d,1H); 6.96(d,2H); 6.85(t,2H); 6.63(m,2H); 6.36(s,1H); 3.87(m, 1H); 3.74(m, 1H); 3.63(m, 1H); 2.72(m,2H); 1.10–2.60(m,28H); 1.30(s,9H).

MS (FAB: m/z 696 ( M+H ).

EXAMPLE 38

(1S-trans-N-(2-Aminocyclohexyl)-3-isoquinolinecarboxamide

The title compound is prepared by the procedure of Example 33 using 1.0 g of 1,2-diaminocyclohexane, 1.0 g of 3-isoquinoline carboxylic acid hydrate, 5.1 g of BOP, 2 ml of triethylamine and 30 ml of methylene chloride to give, after chromatography, 0.668 g of the desired product.

$^2$H NMR(CDCL$_3$):d 9.03(s,1H); 8.73(s,1H); 8.26(d,1H); 7.94(m,2H); 7.68(m,2H); 3.91(m, 1H); 3.38(s,2H); 2.78 (m, 1H); 2.07 (m, 2H); 1.78 (m, 2H); 1.35 (m, 1H).

EXAMPLE 39

[3S-[2[alphaR*[1R*,1(2R*)]],3alpha,4abeta,8abeta]]3-[[(1,1-Dimethylethyl)amino]carbonyl]octahydro-N-[2[(2[(3-isoquinolinylcarbonyl)amino]cyclohexyl]-gamma-methylene-alpha-(phenylmethyl)-2(1H)-isoquinolinepentanamide The title compound is prepared by the procedures of Example 19 and 20. Following Example 19: 0.094 g of product from Example 18, 0.013 g of lithium hydroxide monohydrate, 0.04 ml of 30% hydrogen peroxide, 4 ml of tetrahydrofuran, 1 ml of water and 0.10 g of sodium sulfite in 1 ml of water are reacted to give intermediate (A). Following Example 20: intermediate (A) is reacted with 0.106 g of product from Example 38, 0.221 g of BOP, 0.5 ml of triethylamine and 10 ml of methylene chloride to give 0.097 g of the desired product.

$^1_H$ NMR(CDCL$_3$):d 9.15(s,1H); 8.47(s,1H); 8.25(d,1H); 8.05(d,1H); 7.94(d,1H); 7.76(m,2H); 6.96(d,2H); 6.78(t,2H); 6.72(d,1H); 6.66(t,1H); 6.64(s,1H); 5.09(s,1H); 4.89(s,1H); 3.88(m, 1H); 3.65(m,1H); 3.02(d,1H); 1.10–2.85(m,29H); 1.28(m,9H).

EXAMPLE 40

[3S-[2alphaS*[1R*,1(2R*)]],3alpha,4abeta,8abeta]]3[[(1,1-Dimethylethyl)amino]carbonyl]octahydro-gamma-hydroxy-gamma-(hydroxyethyl)-N-[2-[(3-isoquinolinylcarbonyl)amino]cycohexyl]-alpha-(phenylmethyl)-2(1H)-isoquinolinepentanamide The title compound is prepared by the procedure of Example 21 using 0.097 g of product from Example 39, 0.071 g of osmium tetoxide, 0.5 ml of pyridine, 20 ml of tetrahydrofuran and 1 ml of water to give, after chromatography, 0.071 g of the desired product.

$^1$H NMR(CDCL$_3$):d 9.15(s,1H); 8.47(s,1H); 8.33(d, 1H); 8.02(d,1H); 7.86(d, 1H); 7.74(m,2H); 6.85–7.05(m,6H); 5.92(s,1H); 3.95(m, 1H); 3.73(m, 1H); 3.37(d,1H); 3.27(d,1H); 3.09(d,1H); 1.10–2.70(m,29H); 1.32(s,9H).

MS(FAB): m/z 726 (M+H).

EXAMPLE 41

[3S-[2[alphaS*[1R*,1(2R*)]],3alpha,4abeta,8abeta]]-3-[[(1,1-Dimethylethyl)amino]carbonyl]octahydro-N-[2-[(3-isoquinolinylcarbonyl)amino]cyclohexyl]-gamma-oxo-alpha-(phenylmethyl)-2(1H)-isoquinolinepentanamide The title compound is prepared by the procedure of Example 22 using 0.046 g of product from Example 40, 0.050 g of sodium periodate, 20 ml of tetrahydrofuran and 0.5 ml of water to give, after chromatography, 0.039 g of the desired product.

¹H NMR(CDCL₃):d 9.15(s,1H); 8.48(s,1H); 8.33(d, 1H); 8.02(d,1H); 7.86(d,1H) ;7.72(m,2H); 6.85–7.05(m,2H); 6.79(d,1H); 6.72(s,1H); 3.96(m,2H); 3.74(m,1H); 3.18(d,1H); 2.50–3.02(m,5H); 2.09(dd,1H); 1.20–2.20(m,23H); 1.17 (s,9H).

EXAMPLE 42

[3S-[2[alphaS*[1R*,1(2R*)]],3alpha,4abeta,8abeta]]-3-[[(1,1-Dimethylethyl)amino]carbonyl)octahydro-gamma-hydroxy-N-[2-[(3-isoquinolinylcarbonyl)amino]cyclohexyl]-alpha-(phenylmethyl)-2-(1H)-isoquinolinepentanamide The title compound is prepared by the procedure of Example 23 using 0.013 g of product from Example 41, 0.020 g of sodium borohydride, 3 ml of tetrahydrofuran and 1 ml of methyl alcohol to give 0.0074 g of the product as a 3/1 mixture of epimers.

Major isomer: ¹H NMR(CDCL₃):d 9.15 (s, 1H); 8.52 (s, 1H); 8.28(d,1H); 8.05(d,1H); 7.95(d, 1H); 7.75(m,2H); 6.97(d,2H); 6.68(m,3H); 6.67(t,1H); 6.40(s,1H); 3.92 (m, 1H); 3.73 (m, 1H); 3.64 (m, 1H); 1.10–2.90 (m, 30 H); 1.32(s,9H).

Minor isomer: ¹H NMR(CDCL₃):d 9.15(s,1H); 8.49(s,1H); 8.28(d,1H); 8.10(d,1H); 7.95(d,1H); 7.75(m,2H); 6.97 (d,2H); 6.81(m,3H); 6.59(t,1H); 6.19 (s, 1H); 3.91(m, 1H); 3.75(m, 1H); 3.67(m,1H); 2.78(m,2H); 1.10–2.58(m,28H); 1.30(s,9H).

EXAMPLE 43

(R)-[2-[(2-Aminophenyl)amino]-1-methyl-2-oxoethyl], -carbamic acid phenylmethyl ester To a 0° C. solution of 10.60 g of N-carbobenzoxy D alanine in 25 ml of tetrahydrofuran is added 8.47 g of carbonyldiimidazole over 0.5 hour. To this solution is added 5.135 g of 1,2-phenylenediamine. The reaction is allowed to warm to room temperature and the stirring continued overnight. The reaction is diluted with water, extracted with diethyl ether and the organic layer is washed with saturated sodium chloride, saturated sodium bicarbonate and water. The organic layer is dried and concentrated in vacuo to give 12.74 g of the desired product.

$[a]_D^{26}$= +13±1.

¹H NMR(CDCL₃):d 8.797(bd,1H); 8,419(bd, 1H); 7.143(m,2H); 6.97(t,1H); 6.639(dt,2H); 6.028(dd,2H); 5.134(m,2H); 4.958(bs,1H); 4,375(m, 1H); 3.75(bs,2H); 1,495(d,3H).

EXAMPLE 44

(R)-[1-(1H-Benzimidazol-2-yl)ethyl]carbamic acid phenylmethyl ester

A mixture of 0.104 g of product from Example 43 and 10 ml of o-xylene is heated at reflux temperature overnight. The reaction mixture is decolorized with charcoal, filtered and concentrated in vacuo to give a dark brown oil. The oil is recrystallized from carbon tetrachloride to give 0.10 g of the desired product.

¹H NMR(CDCL₃):d 7.0–7.6(mm,9H); 5.175(m,2H); 4.376(bm, 1H); 1,695(d,3H).

EXAMPLE 45

(R)-alpha-Methyl-1H-benzimidazole-2-methanamine

The title compound is prepared by the procedure of Example 15, in a Parr apparatus, using 1.07 g of product from Example 44, 90 ml of methyl alcohol and 2.45 g of 10% palladium on carbon to give 0.48 g of the desired product after recrystallization from carbon tetrachloride.

¹H NMR(CDCL₃):d 7.0–7.6(mm,4H); 4.415(m, 1H); 1.553(d,3H).

EXAMPLE 46

[1S-1R*(R(R*),2R*]]-[1-[[[1-(1H-Benzimidazol-2-yl)ethylamino]carbonyl]-2-methylbutyl]carbamic acid 1,1-dimethylethyl ester The title compound is prepared by the procedure of Example 1 using 0.0533 g of product from Example 45, 0.0765 g of N-t-Boc-L-isoleucine, 0.293 g of BOP, 0.14 ml of triethylamine and 10 ml of methylene chloride to give, after chromatography, 0.0383 g of the desired product.

¹H NMR(CDCL₃):d 7.563(m,2H); 5.78(m, 1H); 5.4(m, 1H); 3.90(m,1H); 1.262(s,9H); 0.6–1.8(mm,10 H).

EXAMPLE 47

[S-(R,R*)]-2-Amino-N-[1-(1H-benzimidazole-2-yl)ethyl]-3-methylpentanamide

A mixture of 0.0393 g of product from Example in a 1:1 solution of trifluoroacetic acid:methylene chloride is heated at reflux temperature overnight. The reaction mixture is concentrated in vacuo to give 0.027 g of the desired product as a brown oil.

EXAMPLE 48

[3S-[2[alphaR*[1R*,1(R*),2R*]],3alpha,4abeta,8abeta]]-N-[1-[[[1-(1H-benzimidazol-2-yl)ethyl]amino]carbonyl]-2-methylbutyl]-3-[[(1,1-dimethylethyl)amino]carbonyl]-octahydro-gamma-methylene-alpha-(phenylmethyl)-2(1H)-isoquinolinepentanamide The title compound is prepared by the procedures of Example 19 and 20. Following Example 19: 0.079 g of product from Example 18, 0.044 g of lithium hydroxide monohydrate, 0.118 ml of 30% hydrogen peroxide, 0.80 ml g of sodium sulfite and 10 ml of water are reacted to give intermediate (A). Following Example intermediate (A) is reacted with 0.145 g of product from Example 47, 0.073 g of BOP, 0.18 ml of triethylamine and 10 ml of methylene chloride to give, after chromatography, 0.030 g of the desired product.

¹H NMR(CDCL₃):d 6.9(mm,10 H); 6.460(d, 1H); 6.42(d,1H); 6.23(s,1H); 5.220(qt,1H); 5.100(bs,1H); 4.920(bs,1H); 4.030(t,1H); 3.18(bd,1H); 1.369(s,9H); 0.9–3.0(mm,33H).

EXAMPLE 49

[3S-[2[alphaS*[1R*,1(R*),2R*]],3alpha,4abeta,8abeta]]-N-[1-[[[1-(1H-benzimidazol-2-yl)ethyl]amino]carbonyl]-2-methylbutyl]-3-[[(1,1-dimethylethyl)amino]carbonyl]-octahydro-gamma-hydroxy-gamma-(hydroxymethyl)-alpha-phenylmethyl-2(1H)-isoquinolinepentanamide The title compound is prepared by the procedure of Example 21 using 0.030 g of product from Example 48, 0.0165 g of osmium tetroxide, 0.175 ml of pyridine,3 ml of tetrahydrofuran, and 0.2 ml of water to give 0.0228 g of the desired product.

¹H NMR(CDCL₃):d 6.2–8.0(mm,12H); 6.90(s,1H); 5.4(m,1H); 4.48(m,1H); 4.1(m, 1H).

EXAMPLE 50

[3S-[2[alphaS*[1R*,1(R*),2R*]],3alpha,4abeta,8abeta]]-N-[1-[[[1-(1H-benzimidazol-2-yl)ethyl]amino]carbonyl]-2-methylbutyl]-3-[[(1,1-dimethylethyl)amino]-carbonyl]octahydro-gamma-oxo-alpha-(phenylmethyl)-2(1H)-isoquinolinepentanamide The title compound is prepared by the procedure of Example 23 using 0.0228 g of product from Example 49, 0.050 g of sodium periodate, 2 ml of tetrahydrofuran and 1 ml of water to give 0.0102 g of the desired product.

$^1$H NMR(CDCL$_3$):d 6.90–7.7(mm,10 H); 6.60(2m,2H); 6.4(s,1H); 5.35(m, 1H); 4.04(m, 1H); 3.3(d,1H); 0.85–3.30(mm,33H); 1.432(s,9H).

EXAMPLE 51

[3S-[2alphaS*[1R*,1(R*),2R*]],3alpha,4abeta,8abeta]]-N-[1-[[[1H-benzimidazol-2-yl)ethyl]amino]carbonyl]-2-methylbutyl]-3-[[(1,1-dimethylethyl)amino]-carbonyl]octahydro-gamma-hydroxy-alpha-phenylmethyl)-2(1H)-isoquinolinepentanamide The title compound is prepared by the procedure of Example 23 using 0.0102 g of product from Example 50, 0.0055 g of sodium borohydride, 1 ml of methyl alcohol and 2 ml of tetrahydrofuran to give 0.0021 g of the desired product.

MS (FAB): m/z 701 (M+H).

We claim:

1. A compound selected from the group consisting of:
   [3S-[2alphaS*(1R*,2R*),gammaR*(and S*)],3alpha,4abeta,8abeta]]-N-[1-[[(1H-Benzimidazol-2-ylmethyl)amino]carbonyl]-2-methylbutyl]-3-[[(1,1-dimethylethyl)amino]-carbonyl]decahydro-gamma-hydroxyalpha-(phenylmethyl)-2-isoquinolinepentanamide;
   [3S-[2[alphaS*(1R*,2R*),gammaR*],3alpha,4abeta,8abeta]]-N-[1[[(1H-benzimidazol-2-ylmethyl)amino]carbonyl]-2-methylbutyl]-3[[(1,1-dimethylethyl)amino]-carbonyl]decahydro-gamma-hydroxy-alpha(phenylmethyl)-2-isoquinolinepentanamide; and
   [3S-[2[alphaS*(1R*,2R*),gammaS*],3alpha,4abeta,8abeta]]-N-[1-[[(1H-benzimidazol-2-ylmethyl)amino]carbonyl]-2-methylbutyl]-3-[[(1,1-dimethylethyl)amino]-carbonyl]decahydro-gamma-hydroxy-alpha-(phenylmethyl)-2-isoquinolinepentanamide.

2. The compound according to claim 1, [3S-[2[alphaS*(1R*,2R*),gammaR*(and S*)],3alpha,4abeta,8abeta]]-N-[1-[[(1H-Benzimidazol-2-ylmethyl)amino]carbonyl]-2-methylbutyl]-3-[[(1,1-dimethylethyl)amino]carbonyl]decahydro-gamma-hydroxy-alpha-(phenylmethyl)-2-isoquinolinepentanamide.

3. The compound according to claim 1, [3S-[2[alphaS*(1R*,2R*),gammaR*],3alpha,4abeta, 8-abeta]]-N-[1-[[(1H-Benzimidazol-2-ylmethyl)amino]carbonyl]-2-methylbutyl]-3-[[(1,1-dimethylethyl)amino]carbonyl]-decahydro-gamma-hydroxy-alpha-(phenylmethyl)-2isoquinolinepentanamide.

4. The compound according to claim 1, [3S-[2[alphaS*(1R*,2R*),gammaS*],3alpha,4abeta, 8abeta]]-N-[1-[[(1H-Benzimidazol-2-ylmethyl)amino]carbonyl]-2-methylbutyl]-3-[[(1,1-dimethylethyl)amino]carbonyl]-decahydro-gamma-hydroxy-alpha-(phenylmethyl)-2isoquinolinepentanamide.

5. A method of inhibiting the in vitro protease enzyme of the HIV retrovirus which comprises contacting said enzyme with an effective amount of a compound according to claim 1.

6. A pharmaceutical composition which comprises an effective amount of a compound according to claim 1 in association with a pharmaceutically acceptable carrier.

* * * * *